US006975231B2

United States Patent
Lane et al.

(10) Patent No.: US 6,975,231 B2
(45) Date of Patent: Dec. 13, 2005

(54) SYSTEMS AND METHODS FOR IMPROVING HAND HYGIENE COMPLIANCE

(75) Inventors: Stephen Lane, McLean, VA (US); Kevin Strauss, McLean, VA (US); Mary Coyne, McLean, VA (US)

(73) Assignee: Amron Corporation, McLean, VA (US)

( * ) Notice: Subject to any disclaimer, the term of this patent is extended or adjusted under 35 U.S.C. 154(b) by 423 days.

(21) Appl. No.: 10/052,354

(22) Filed: Jan. 23, 2002

(65) Prior Publication Data

US 2003/0030562 A1 Feb. 13, 2003

Related U.S. Application Data

(60) Provisional application No. 60/263,159, filed on Jan. 23, 2001.

(51) Int. Cl.[7] ............................................. G08B 23/00
(52) U.S. Cl. ................. 340/573.1; 340/539; 340/545; 340/691; 340/603
(58) Field of Search ................... 340/573.1, 539, 340/603, 691, 661, 541, 567, 545

(56) References Cited

U.S. PATENT DOCUMENTS

| | | | | |
|---|---|---|---|---|
| 4,896,144 A | * | 1/1990 | Bogstad | 340/691.6 |
| 4,986,144 A | * | 1/1991 | Kobayashi et al. | 74/606 |
| 5,202,666 A | * | 4/1993 | Knippscheer | 340/573.1 |
| 5,812,059 A | * | 9/1998 | Shaw et al. | 340/573.1 |
| 5,857,228 A | * | 1/1999 | Waltenberger et al. | 4/662 |
| 5,870,015 A | * | 2/1999 | Hinkel | 340/573.1 |
| 5,945,910 A | * | 8/1999 | Gorra | 340/573.1 |
| 6,028,520 A | * | 2/2000 | Maehre | 340/573.1 |
| 6,727,818 B1 | * | 4/2004 | Wildman et al. | 340/573.1 |

OTHER PUBLICATIONS

Lane—(CRISP) "Computer Retrieval of Information on Scientific Project", Abstract Display—Aug. 2, 2004.

* cited by examiner

*Primary Examiner*—Jeffery Hofsass
*Assistant Examiner*—Daniel Previl

(57) ABSTRACT

A method and apparatus that systematically prompts staff, patients and visitors at care facilities to perform handwashing at critical time periods, for example after touching a toilet flush handle or upon entering or leaving a patient's room. A plurality of detectors are used to sense whether a person has entered an area and to determine whether the person has cleansed their hands within a predetermined period of time before entering the area or leaving the area. If it is determined that the person has cleansed their hands within the predetermined period of time, no prompting message is generated. If it is determined that the person has not cleansed their hands within the predetermined period of time, an audio/visual warning message is generated.

12 Claims, 6 Drawing Sheets

SYSTEMS AND METHODS FOR IMPROVING HAND HYGIENE COMPLIANCE

This patent application claims benefit of U.S. Provisional Patent Application Ser. No. 60/263,159, filed Jan. 23, 2001.

FIELD OF THE INVENTION

The present invention relates to an automated prompting device that increases the frequency of handwashing and decreases infection rates.

BACKGROUND OF THE INVENTION

Infections, including nosocomial infections, are prevalent in all patient care facilities including hospitals and nursing homes. These infections pose a significant health risk to hospitalized patients by delaying healing, extending the length of hospitalization and increasing the human and financial cost of care. A nosocomial infection has been defined as "a localized or systemic condition that 1) resulted from adverse reaction to the presence of an infection agent or its toxin and 2) was not present or incubating at the time of admission to the hospital." Research reveals that several types of microorganisms can be transferred by hand to live hosts, thereby producing nosocomial infections.

Nosocomial infections delay healing, extend the length of hospitalization and increase the cost of care. Each year, approximately 2.4 million Americans acquire a nosocomial infection and 100,000 persons die as a result of such infections.

Handwashing is the linchpin of infection control. Failure to conduct handwashing after toileting or prior to contact with a patient places patients and health care workers at great risk for the development of nosocomial infections. While health care workers play a powerful role in reducing nosocomial infections, they have also been implicated in contributing to their increase by failing to perform handwashing prior to contact with a patient and after handling contaminated materials. Although health care workers are required to participate in annual infection control in service inspections, there is a discrepancy between classroom knowledge and applied knowledge of infection control. This discrepancy suggests that innovative strategies in infection control must be created in order to reduce the rate of nosocomial infections.

U.S. Pat. No. 5,945,910 discloses a handwashing and monitoring system that uses a sensor that signals the dispensation of a cleaning agent from a dispenser. A dual mode monitoring and reporting module includes an input element, an output element, a processor and memory. The module accepts data identifying an employee, receives a signal indicating dispensation of the cleaning agent and stores compliance data records.

U.S. Pat. No. 5,870,015 discloses an apparatus in which toilet use is monitored and audible messages are produced that instruct users of the toilet regarding steps in toilet use and hygiene. The apparatus includes a housing that is removably attached to the toilet. A switch arm is coupled with the toilet handle and sends an activity signal indicative of the switch arm position to electronic circuitry that activates the audible messages.

U.S. Pat. No. 5,812,059 discloses a method and system for enhancing hygiene. An activating device is located outside a work area, a hand cleaning station is located near the work area, and a deactivating device is associated with the hand cleaning station. Upon leaving a food handling area, an indicator worn by a worker is activated when the worker is near the activating device. The indicator is deactivated only when it is determined that the worker has used the hand cleaning station.

U.S. Pat. No. 5,202,666 discloses an automated device used to remind employees to wash their hands after toileting. Sensors are worn on credit card sized badges and mounted in bathroom ceilings and attached to soap dispensers and sinks. When an employee enters the bathroom, the ceiling unit sensor activates a blinking light on the badge. The light is deactivated once the employee pumps the soap dispenser and stands in front of the sink for at least 15 seconds.

U.S. Pat. No. 4,986,144 discloses a hand washing alert warning system designed to warn someone to wash their hands. A door activate system is armed when the door to the wash facility is opened or a toilet is flushed and is deactivated when it is determined that the person has washed their hands.

However, these existing systems have several problems associated with them. For example, they are relatively complex, there is no way to effectively force employees to wear badges, the batteries in the badges have to be replaced frequently and there is no way to monitor what an employee does between the time they wash their hands and the time they return to their work area.

SUMMARY OF THE INVENTION

The present invention provides a method that includes sensing a person in a first area and determining whether the person has cleansed their hands before leaving the area. If it is determined that the person has cleansed their hands, this information is sent to a database. If it is determined that the person has not cleansed their hands before leaving the first area, it is then determined whether the person has entered a second area. If it is determined that the person has entered the second area, it is then determined whether the person has cleansed their hands. If it is determined that the person has not entered the second area, it is then determined whether the person has cleansed their hands in a third area after leaving the first area. If it is determined that the person has cleansed their hands after entering the second or third area, this information is sent to the database. If it is determined that the person has not cleansed their hands after entering the second area or the third area, a warning is generated. Additionally, if it is determined that the person has not cleansed their hands after the warning is generated, this information is sent to the database.

The present invention also includes an apparatus having a central processor for increasing the frequency of handwashing. The present invention includes a receiver and a communication link connecting the central processor and the receiver. A first sensor is located near the opening of a first area for determining entry and exit from the first area. A second sensor is located inside the first area for determining movement within the first area. A module is located inside the first area for emitting audio and visual signals. A third sensor is located at an opening of a second area located adjacent to the first area for determining entry and exit from the second area. A fourth sensor is located inside the second area for determining toilet usage. A fifth sensor is located inside the second area for determining sink usage. A sixth sensor is located near the opening of the first area for determining cleanser dispenser usage. The sensors communicate with the receiver via radio waves and the module communicates with the central processor via the AC power lines.

BRIEF DESCRIPTION OF THE DRAWINGS

This invention will be described in detail with reference to the accompanying drawings wherein.

DETAILED DESCRIPTION OF THE INVENTION

Figure 1:
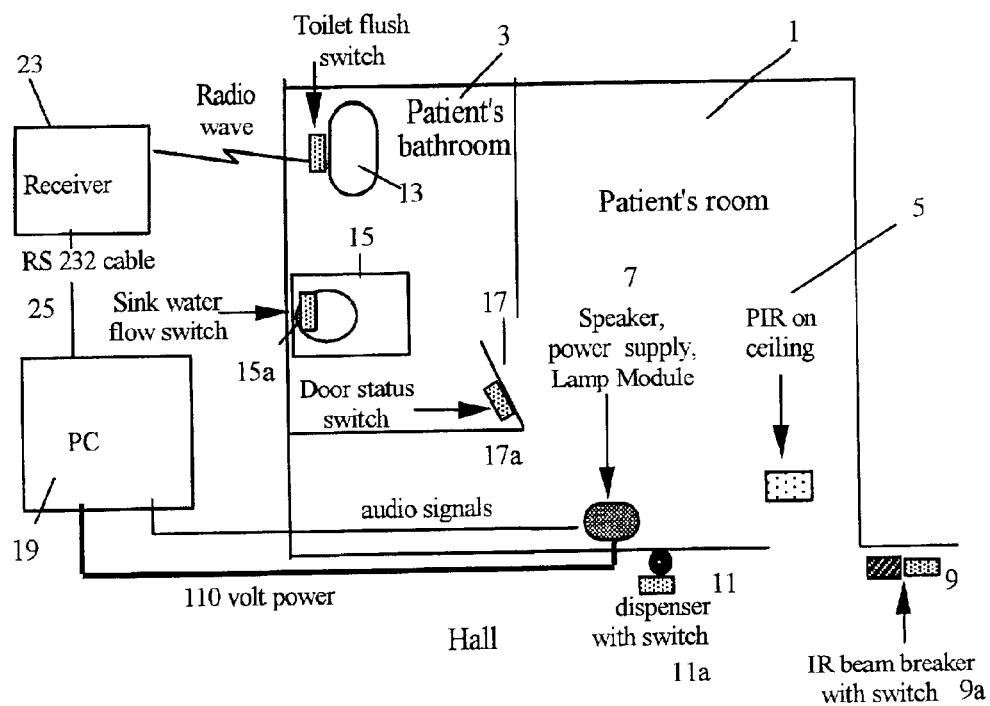
FIG. 1 is an illustration of the patient room with an adjoining bathroom according to a preferred embodiment of the present invention.

FIG. 1 illustrates a schematic view of a system according to a preferred embodiment of the present invention. The system includes patient room 1 and adjoining bathroom 3. As shown, located in patient room 1 is a passive infrared motion (PIR)/thermal detector 5 and a speaker/appliance module assembly 7. Located proximate to patient room 1 is an infrared (IR) beam breaker 9/switch 9a and a dispenser 11/switch 11a. Located inside bathroom 3 is toilet 13/switch 13a, sink 15/water flow switch 15a and bathroom door 17/door status switch 17a. Computer 19 is connected via conventional modes such as radio waves or radio frequency signals (RF) to switches 9a, 11a, 13a, 15a, 17a and PIR 5. Receiver 23 is connected to computer 19 via a standard communications connection 25 such as RS-232.

In a preferred embodiment, door status switch 17a transmits a signal to computer 19 indicating whether bathroom door 17 is open or closed, the toilet flush switch 13a transmits to computer 19 when the toilet handle has been depressed, the sink water flow switch 15a transmits to computer 19 when water is flowing from the sink faucet, and the dispenser switch 11a transmits to computer 19 when the dispenser 11 is used.

IR beam breaker 9 comprises for example, an infrared transmitter with a receiver located on one side of the door and a reflector located on the other side of the door. The detector 5 detects motion inside patient room 1. An IR beam is transmitted across the door, reflected at the other side, and detected at the transmitter to indicate that a person has crossed the threshold. Alternatively, other detection devices such as pressure sensitive floor mats with electrical contacts or other appropriate sensing configurations may be used instead of IR beam breaker 9.

In a preferred embodiment, to detect toilet use, toilet flush switch 13a is attached to the toilet tank with a magnet on the handle for tank type toilets. The magnet and switch 13a are arranged so that flushing the toilet moves the magnet near the switch 13a, triggering a signal to computer 19 that the toilet has been flushed. Alternatively, for toilets that flush by operation of a handle protruding from a pipe that can be moved in any direction to flush the toilet, a thin conductive sheet of metal may be wrapped around the toilet handle. The conductive sheet of metal is electrically insulated from the toilet handle. Wires from the insulated metal sheet and from the pipe into which the handle fits are connected to switch 13a. When the toilet 13 is flushed the conductive metal sheet touches the pipe, completing an electrical circuit. Switch 13a then sends a signal to computer 19 that the toilet 13 has been flushed.

In a preferred embodiment, sink water flow switch 15a is a non-conducting sleeve attached to the sink faucet including electrodes placed inside. The electrodes are electrically isolated from the aerator body and are placed directly in the water stream when the water is flowing. Ordinary tap water is conductive because of dissolved electrolytes and therefore, water flowing over the electrodes conducts enough current between them to close the sink water flow switch 15a. Thus, a signal from the switch 15a indicates water flowing in the sink indicating handwashing. In another embodiment, handwashing may be inferred from use of a dispenser 11/switch 11a located near sink 15 that is used to directly sense the dispensation of a cleanser, such as soap and to provide the appropriate signal to computer 19.

The dispenser 11 consists of a tube containing for example, liquid alcohol-based foam and has a downward pointing spout on the bottom and may be mounted in a bracket on the wall adjacent patient room 1. To detect foam dispensing, the dispenser's spout may be attached to a switch 11a or switch 11a may be placed on the wall behind the foam-dispensing nozzle, in such a way that a person dispensing foam will press switch 11a. The foam dispenser may be mounted on a bracket on microswitches, which are mounted on the wall and connected in parallel to switch 11a. Alternately, a pressure actuated switch may be mounted on the wall in such a way that a person must press it to dispense foam. When a person presses the foam dispenser nozzle one or more microswitches close. The switches are connected to a status switch that transmits a signal indicating foam use to the computer. In yet another embodiment, a thermal detector may be mounted under the foam dispenser to note when a person places their hands on the spout to dispense foam.

At least one computer is used to implement the present invention. The computer receives and processes data from all sensors. Alternatively, additional computers may be used as required if the radio waves from the sensors are not strong enough to penetrate the walls between the computer and the most distant hospital rooms. In this case the additional computers are installed at separate locations from the first computer. Each computer can process data from specific areas.

In a preferred embodiment the computer 19 communicates with sensors/switches via RF signals. However, it should be understood that radio waves may be replaced by higher frequency signals, optical signals, hard wires, or any well known communications system or method.

In a preferred embodiment, thermal detector 5 is an infrared motion detector that detects time variations in differences in temperature in different directions in the detectors field of view. The device observes the energy radiated by objects in their vicinity, but do not emit any radiation of their own, except for the RF signals transmitted to computer 19. When the thermal detector detects motion, an RF signal is sent indicating the detector's new state and a unique address. The switches and sensors preferably contain a radio transmitter that transmits their unique address and a signal indicating an "on" status when their terminals are closed and a signal indicating an "off status when those terminals are opened. Receiver 23 detects the signal and transmits it to computer 19 via RS-232 cable or any well know communication means. Computer 19 can then determine which switch changed state, and the new state as well.

Figure 2:
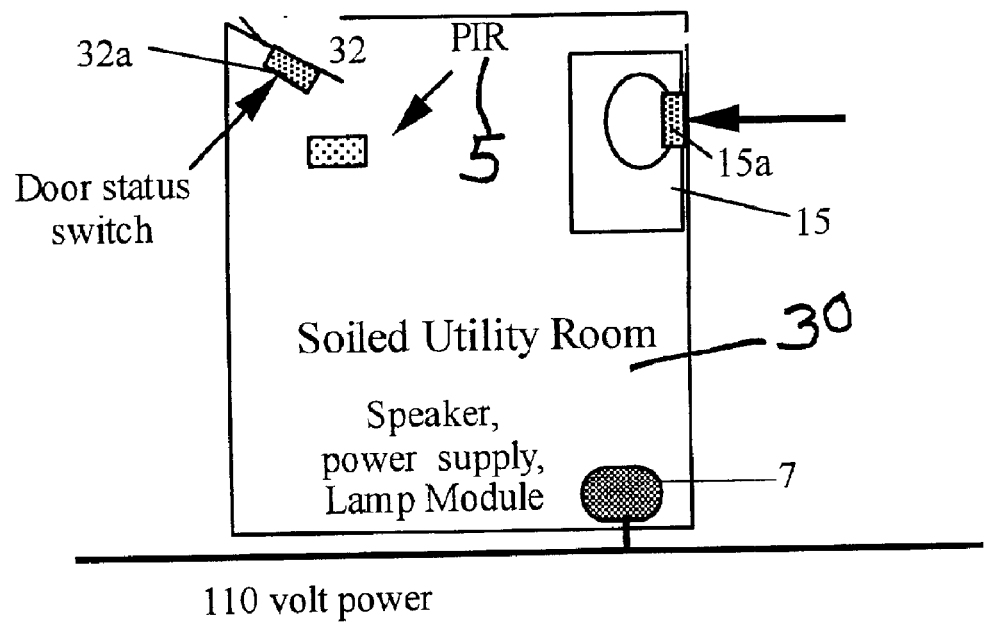
FIG. 2 is an illustration of a non-patient room according to a preferred embodiment of the present invention.

FIG. 2 is a schematic of a soiled utility room 30 illustrating a further usage of the present invention. As shown, located in the room is a detector 5, a sink 15/water flow switch 15a, and a speaker/power supply/appliance module 7.

Attached to door 32 is door status switch 32a. A message is played in the soiled utility room 30 reminding those leaving the room to wash their hands if they open the door to leave without having washed their hands. Additionally, door status switch 32a may be used with an IR beam or an outer floor mat.

Figure 3:
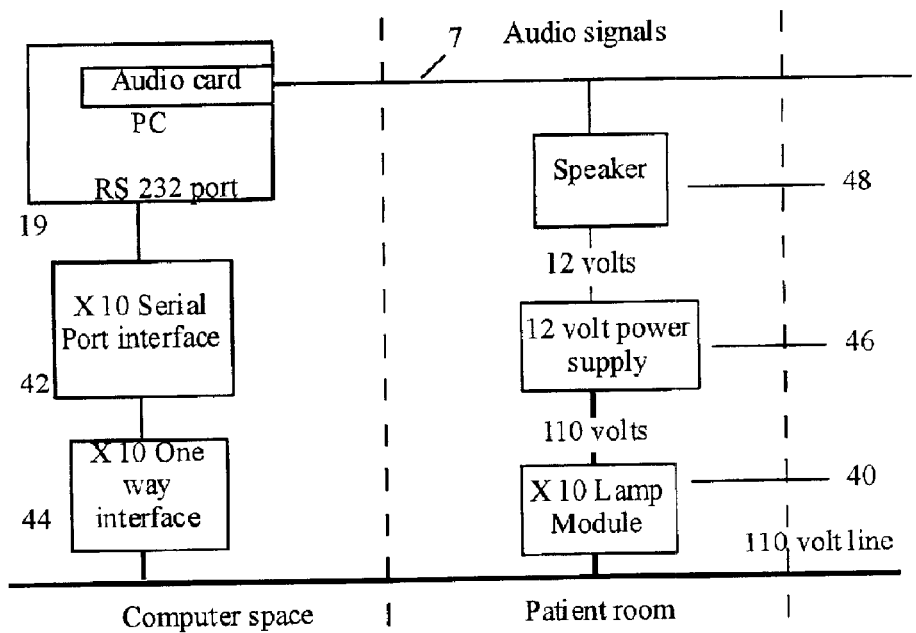
FIG. 3 is an illustration an audio message delivery system according to another embodiment of the present invention.

One embodiment of the speaker/power supply/appliance module 7 is illustrated in FIG. 3. A module 40 such as the X10 by Home Automation Systems™, Inc., is connected to an ordinary 110 volt wall socket. The signal is sent from computer 19 using the X10 Serial Port Interface 42 and the X10 Interface 44 shown in communication between computer 19 and the 110 volt line. A 12-volt DC power supply 46 is connected to module 40. The power supply output cable is connected to the power socket speaker 48. Alternatively, a flashing lighted sign may also be connected to module 40.

Figure 4A:
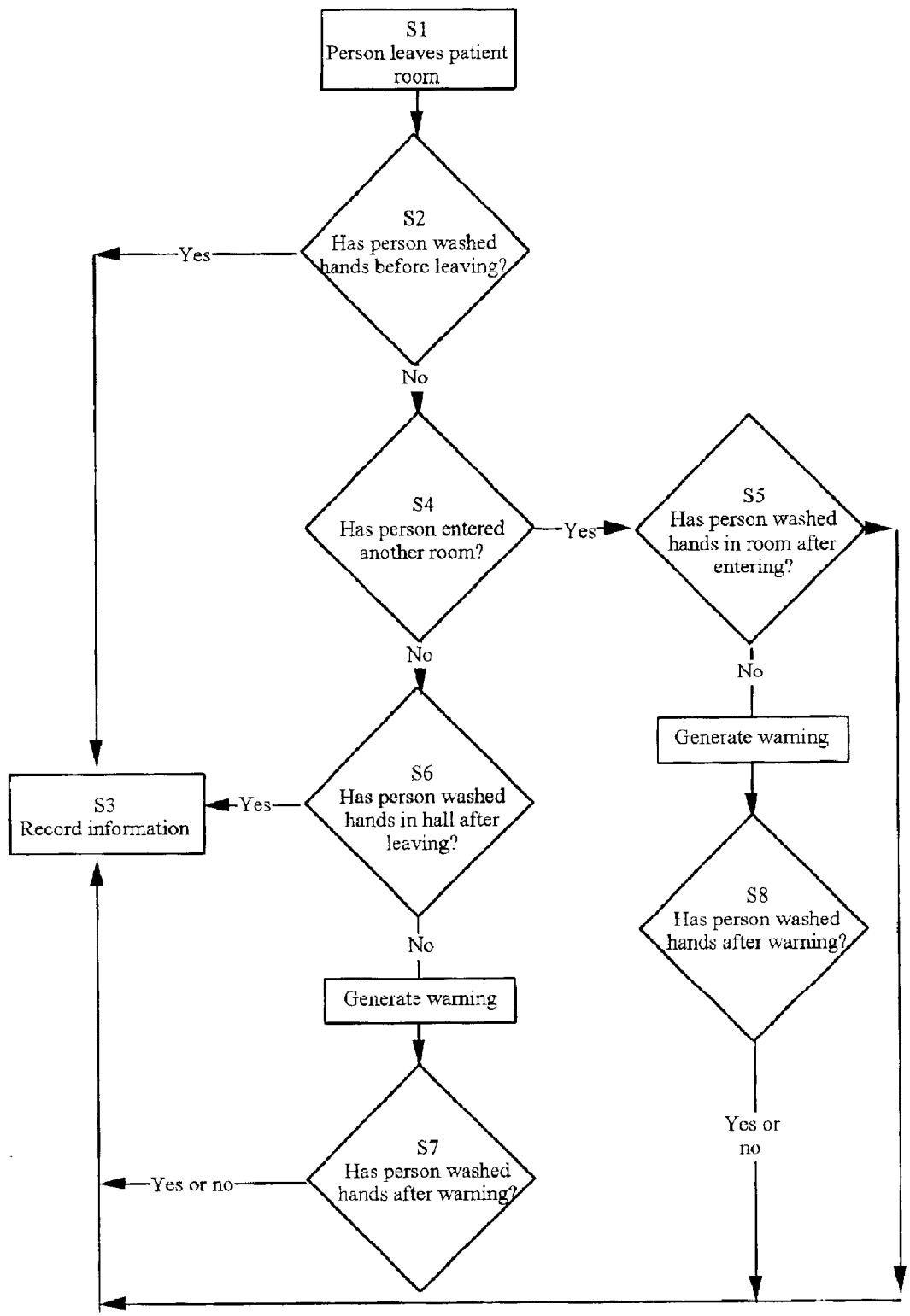
FIGS. 4a, 4b and 4c are flowcharts illustrating the process steps for FIGS. 1 and 2.
Figure 4B:
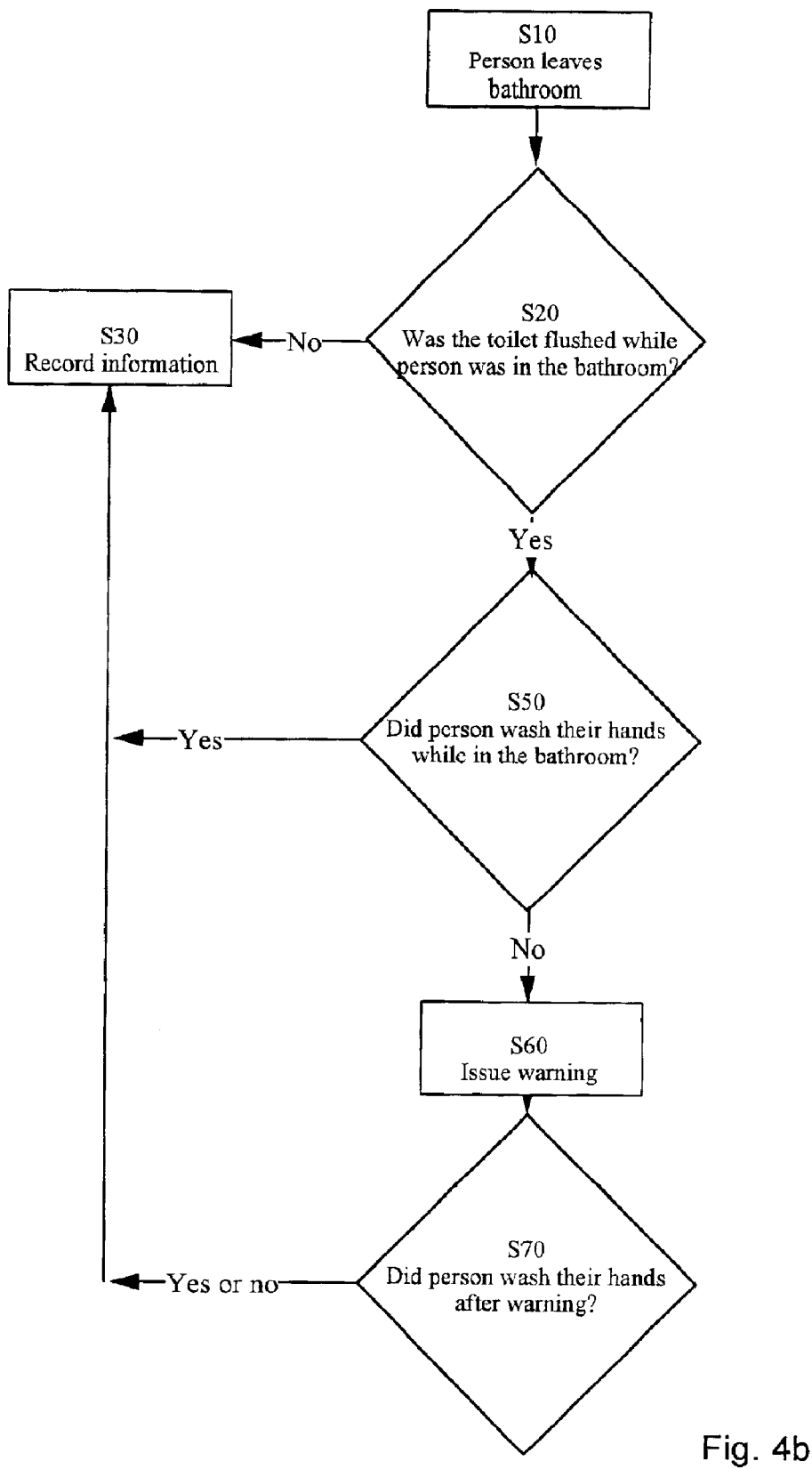
Figure 4C:
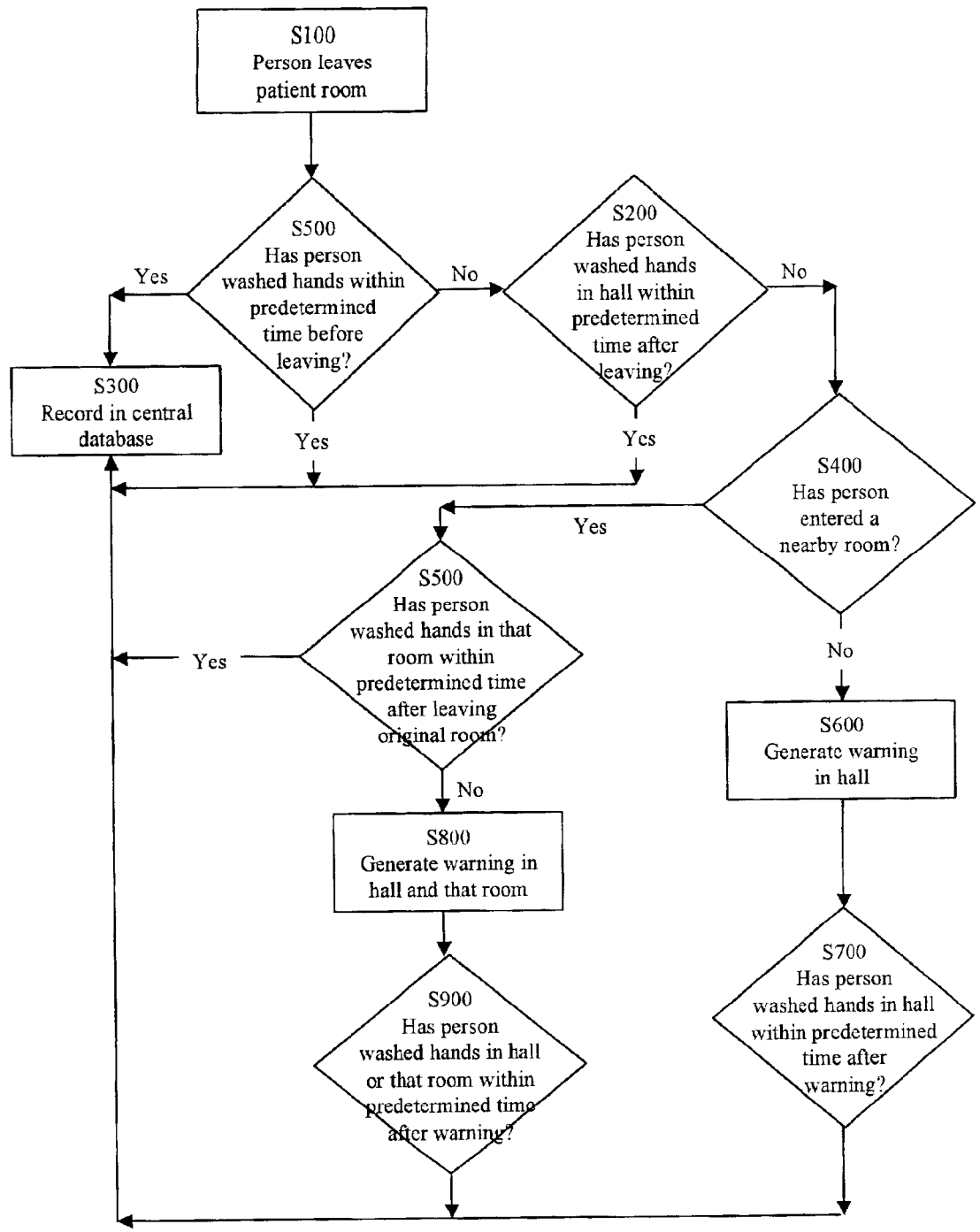

FIGS. 4a, 4b and 4c are flowcharts illustrating the systems of FIGS. 1 and 2. As shown in FIG. 4a, when a person leaves the patient room at Step S1, and if it is determined at Step S2 that the person washed their hands within a predetermined time before leaving the room, this information is recorded at Step S3 and no warning is given. If it is determined at Step S4 that a person did not wash their hands at Step S2 but instead entered a nearby room, then at Step S5 it is determined if they washed their hands in that room after a predetermined time. If is determined at Step S4 that the person did not enter another room but at Step S6 it is determined that the person did wash their hands in another area such as the hall after a predetermined time, then this information is recorded in Step S3 and no warning is given. If it is determined at Step S5 that the person washed their hands after a predetermined time in the second room then this information is sent to the central database at Step S3 and no warning is issued. If it is determined at Step S5 that the person did not wash their hands in the second room after a predetermined time, then a warning is issued for example, in the hall and in the room. At Step S8, if it is determined that the person washed their hands after the warning, this information is sent the database at Step S3. If it is determined at Step S7 that the person washed their hands in the hall after the warning, this information is sent to the database at Step S3.

As shown in FIG. 4b, when a person leaves the bathroom at Step S10, and it is determined at step S20 that they flushed the toilet while in the bathroom, and it is also determined that the person washed their hands in the bathroom at Step S50, then no prompt is issued and the information is recorded at Step S30. If it is determined at Step S50 that a person used the toilet in Step S20, but that the person did not wash their hands before leaving the bathroom at Step S10, an appropriate warning, such as "wash your hands please" is issued at Step S60. It is then determined at Step S70 if the person washed their hands in response to this prompt and the information is recorded at Step S30. If it is determined at Step S50 that a person used the toilet and subsequently flushed the toilet, then a warning is issued at Step 60 if the person has not washed their hands after the last flush, even if they have washed their hands after a previous flush.

As shown in FIG. 4c, when a person leaves the patient room at Step S100, and if it is determined at Step S500 that the person washed their hands before leaving the room, this information is recorded at Step S300 and no prompt is given. If the person does not wash before leaving the room and it is determined at Step S200 that the person washed their hands after leaving the room, then this information is recorded at Step S300 and no prompt is issued. If it is determined that the person did not wash their hands at Step S200 but entered a nearby room at Step S500, it is determined whether they washed their hands in that room. If is determined at Step S500 that the person washed their hands in the second room, this information is sent to the central database at Step S300 and no prompt is issued. If it is determined that the person did not wash their hands at Step S500, a warning prompt is issued in the hall and in that room as Step S800. At Step S900, if it is determined that the person thereafter washed their hands. This information is sent to the central database. If it is determined at Step S400 that the person did not enter another room, a warning prompt is issued in the hall at Step S600. If it is subsequently determined at Step S700 that the person thereafter washed their hands, this information is sent to the database at Step S300.

For example, when a person leaves the soiled utility room 30 illustrated in FIG. 2, if the person has already washed their hands, then only a record of the event is made. If the person has not washed their hands, when they leave they will hear a verbal prompt such as "wash your hands, please."

In one embodiment, verbal prompts or audible prompts are used. However, although verbal prompts are effective, they may disturb patients. Verbal prompts can be used in areas such as the soiled utility room and staff bathroom and similar rooms without patients. Alternatively, visual prompts, such as flashing lights, may also be used. For example, a flashing light or flashing lighted sign may be used at all times and verbal prompts during daylight. Visual prompts may be used in rooms where voices are objectionable. Additionally, any combination of visual, audible, sensory, vibrating, or any other appropriate prompt is within the scope of the invention.

Computer 19 is preferably equipped to convert digital files into an analog representation of speech. The audio signal is transmitted to speakers in hospital rooms and hallways via low voltage wires. Multiple speakers are controlled from a single computer, sending a message to one or more speaker at a time. In a preferred embodiment, messages are sent from the computer to the speakers via radio waves. Messages may be sent to just one speaker via radio waves having a frequency detected by one particular speaker.

In the preferred embodiment, data is collected and files are edited via a dedicated telephone line in communication with a central location. Computer 19 communicates with a computer at the central location so as to allow remote editing of files and remote data collection from computer 19 without physically being present at the patient facility. Alternatively, data may be collected and files edited on site.

The present invention determines when a person enters or leaves an area by comparing the sensor turn on times according to Table 1 and Table 2. Table 1 shows the sensor status when a person enters the room from the hall. "X" indicates time on the order of 5 seconds in the preferred embodiment, but is adjustable.

TABLE 1

| Entry to room from hall | | |
|---|---|---|
| Sensor\Status | On now? | On within the last X seconds? |
| IR Beam Breaker 9 | No | Yes |
| Detector 5 | Yes | Irrelevant |

In Table 1, the IR beam breaker 9 indicates that an object was in the door way within the last X seconds and detector 5 indicates that there is now something just inside the doorway.

TABLE 2

Exit from room to hall

| Sensor\Status | On now? | On within the last X seconds? |
|---|---|---|
| IR Beam Breaker 9 | Yes | Irrelevant |
| Detector 5 | No | Yes |

In Table 2, IR beam 9 is activated, indicating that a person is in the doorway. Detector 5 is shown as being activated within the last X seconds, indicating that a person has recently been just inside the patient's door.

Various embodiments of the invention have been disclosed herein. According to the present invention, a device senses a person entering into a room. A determination is made as to whether the person has cleansed their hands within a predetermined period of time. If it is determined that the person has cleansed their hands, the information is sent to a database. If it is determined that the person has not cleansed their hands, a warning signal is generated and as a result, the person is prompted to cleanse their hands.

Although various embodiments have been discussed, it is to be understood that while certain forms of the present invention, such as means for signaling, audio/visual warnings, have been illustrated, the invention is not to be limited to the specific forms or arrangements of parts described or shown. Although an inpatient environment has been described herein, the method and system is also applicable to other environments where hygiene is important such as food service or day care facilities. Given the above disclosure, many other features, modifications and improvements will become apparent to one skilled in the art.

What is claimed is:

1. A method of improving hand hygiene compliance, comprising the steps of:
   (a) maintaining a computer database;
   (b) determining whether any person entered a first area independent of whether the any person includes a sensor;
   (c) determining whether the any person left the first area and entered a second area
   (d) determining whether the any person washed their hands before leaving the first area;
   (e) if it is determined that the any person washed their hands before leaving the first area, sending this information to the computer database;
   (e) if it is determined that the any person did not wash their hands before leaving the first area, determining whether the any person washed their hands in the second area;
   (f) if it is determined that the any person washed their hands in the second area, sending the information to the computer database;
   (g) if it is determined that the any person did not wash their hands in the second area, generating at least one of a warning and a reminder; and
   (h) if it is determined that the any person did not wash their hands after the at least one of the warning and the reminder is generated, sending the information to the computer database.

2. The method of claim 1, wherein the step of generating at least one of the warning and the reminder comprises the step of generating at least one of the warning and the reminder when after the any person enters the second area without washing their hands in the first area, a predetermined amount of time expires without the any person washing their hands in the second area.

3. The method of claim 1, wherein the at least one of the warning signal and the reminder comprises at least one of an audio signal and a visual signal.

4. A method of improving hand hygiene compliance, comprising the steps of:
   determining whether any person flushed at least one of a restroom toilet and a soil room waste disposer;
   if the any person flushed the at least one of the restroom toilet, and the soil room waste disposer, determining whether the any person washed their hands within a predetermined amount of time after flushing the at least one of the restroom toilet and the soil room disposer;
   if it is determined that the any person did not wash their hands within the predetermined amount of time after flushing the at least one of the restroom toilet and the soil room disposer, generating at least one of a warning signal and a reminder and sending this information to the central database; and
   if it is determined that the any person did not wash their hands after the at least one of the warning signal and the reminder was generated, sending this information to the central database.

5. The method of claim 4, wherein the at least one of the warning signal and the reminder comprises at least one of an audio signal and a visual signal.

6. An apparatus for improving hand hygiene compliance, comprising:
   means for detecting, wherein the means for detecting is configured to detect each of:
      whether any person entered a first area independent of whether the any person includes means for communicating with the means for detecting; and
      whether the any person left the first area and entered a second area independent of whether the any person includes means for communicating with the means for detecting;
   means for determining whether the any person washed their hands before leaving the first area;
   means for determining whether the any person washed their hands in the second area after leaving the first area; and
   means for generating at least one of a warning and a reminder when the any person does not wash their hands in the second area after leaving the first area without washing their hands in the first area.

7. The apparatus of claim 6, wherein the means for detecting comprises an IR beam breaker switch.

8. The apparatus of claim 6, wherein the at least one of the warning and the reminder comprises at least one of an audio signal and a visual signal.

9. A system for improving hand hygiene compliance, comprising:
   means for determining whether any person flushed at least one of a restroom toilet and a soil room waste disposer;
   means for determining whether the any person washed their hands within a predetermined amount of time after flushing the at least one of the restroom toilet and the soil room waste disposer;
   means for generating at least one of a warning signal and a reminder when the any person flushes the toilet and does not wash their hands within the predetermined amount of time after flushing the at least one of the restroom toilet and the soil room waste disposer; and means for transmitting to a central database information associated with whether or not the any person washed their hands after flushing the at least one of the restroom toilet and the soil room waste disposer.

10. The system of claim 9, wherein the at least one of the warning signal and the reminder comprises at least one of an audio signal and a visual signal.

11. A method of improving hand hygiene compliance, comprising the steps of:

determining whether any person closed a door independent of whether the person includes a sensor, wherein the door divides a first area from a second area, the second area has at least one of a toilet and a waste disposer located therein, and the any person closed the door after entering the second area from the first area;

determining whether the any person flushed the at least one of the toilet and the waste disposer;

if the any person flushed the at least one of the toilet and the waste disposer, determining whether the any person washed their hands before opening the door to leave the second area;

if it is determined that the any person did not wash their hands before opening the door to leave the second area, generating at least one of a warning signal and a reminder and sending this information to the central database; and if it is determined that the any person did not wash their hands after the at least one of the warning signal and the reminder was generated, sending this information to the central database.

12. A system for improving hand hygiene compliance, comprising:

means for determining whether any person closed a door independent of whether the any person includes means for communicating with the means for determining whether the any person closed the door, wherein the door divides a first area from a second area, the second area has at least one of a toilet and a waste disposer located therein, and the any person closed the door after entering the second area from the first area;

means for determining whether the any person flushed the at least one of the toilet and the waste disposer;

means for determining whether the any person washed their hands before opening the door to leave the second area;

means for generating at least one of a warning signal and a reminder when the any person flushes the at least one of the toilet and the waste disposer and does not wash their hands before opening the door to leave the second area; and means for transmitting to a central database information associated with whether or not the any person washed their hands before opening the door to leave the second area.

* * * * *